(12) United States Patent
Bloomfield (10) Patent No.: US 7,391,015 B2
(45) Date of Patent: Jun. 24, 2008

(54) SYSTEM AND METHOD FOR DATA COLLECTION IN RECURSIVE MASS ANALYSIS

(75) Inventor: Nicholas Bloomfield, Newmarket (CA)

(73) Assignees: MDS Analytical Technologies, Concord, Ontario (CA); Applera Corporation, Framingham, MA (US)

( * ) Notice: Subject to any disclaimer, the term of this patent is extended or adjusted under 35 U.S.C. 154(b) by 202 days.

(21) Appl. No.: 11/421,854

(22) Filed: Jun. 2, 2006

(65) Prior Publication Data

US 2008/0067340 A1 Mar. 20, 2008

Related U.S. Application Data

(60) Provisional application No. 60/686,918, filed on Jun. 3, 2005.

(51) Int. Cl.
*B01D 59/44* (2006.01)
*H01J 49/00* (2006.01)

(52) U.S. Cl. .................. 250/281; 250/282; 250/288; 250/283; 250/492.3; 250/252.1; 435/68.1; 435/7.1; 435/4; 435/183; 436/518; 702/19; 702/23; 702/24

(58) Field of Classification Search ............. 250/281, 250/282, 288, 283, 492.3, 252.1; 435/68.1, 435/7.1, 4.183; 436/518; 702/19, 23, 24

See application file for complete search history.

(56) References Cited

U.S. PATENT DOCUMENTS

| | | | |
|---|---|---|---|
| 4,234,791 A | 11/1980 | Enke et al. | |
| 4,861,988 A | 8/1989 | Henion et al. | |
| 4,963,736 A | 10/1990 | Douglas et al. | |
| 5,248,875 A | 9/1993 | Douglas et al. | |
| 6,015,972 A | 1/2000 | Hager | |
| 6,111,250 A | 8/2000 | Thomson et al. | |
| 6,124,591 A | 9/2000 | Schwartz et al. | |
| 6,140,638 A | 10/2000 | Tanner et al. | |
| 6,177,668 B1 | 1/2001 | Hager | |

(Continued)

FOREIGN PATENT DOCUMENTS

CA 2440511 9/2002

(Continued)

OTHER PUBLICATIONS

Haller, et al., Collision Induced Decomposition of Peptides. Choice of Collision Parameters, J. Am. Soc. Mass Spectrum, vol. 7, 1996, pp. 677-681 (5 pages).

(Continued)

*Primary Examiner*—Jack I. Berman
*Assistant Examiner*—Meenakshi S Sahu
(74) *Attorney, Agent, or Firm*—Torys LLP (57) ABSTRACT

Systems, methods, and computer programming for collecting data using a mass spectrometer comprising a particle detector or other mass analyzer. A data collection such as a tree or array structure which includes data records for storing detected data is maintained in volatile or persistent memory. Data is received from the mass analyzer. Whether the collection contains data records corresponding to newly-acquired data signals is determined. If the collection does not contain records corresponding to the newly-received records, a new record is added. In either case, the record corresponding to the received data record is updated to reflect reception of the newly-acquired signal.

10 Claims, 10 Drawing Sheets

U.S. PATENT DOCUMENTS

| | | |
|---|---|---|
| 6,720,554 B2 | 4/2004 | Hager |
| 7,199,361 B2 | 4/2007 | Bloomfield et al. |
| 2003/0122071 A1 | 7/2003 | Plomley et al. |
| 2003/0168589 A1 | 9/2003 | Hager |
| 2003/0189168 A1 | 10/2003 | Londry et al. |
| 2003/0189171 A1 | 10/2003 | Londry et al. |
| 2003/0235628 A1 | 12/2003 | Taneja et al. |
| 2005/0001160 A1 | 1/2005 | Wall |
| 2005/0277789 A1 | 12/2005 | Bloomfield et al. |
| 2007/0158542 A1 * | 7/2007 | Bauer et al. ............. 250/282 |

FOREIGN PATENT DOCUMENTS

| | | |
|---|---|---|
| CA | 2452128 | 1/2003 |
| CA | 2482095 | 3/2003 |
| CA | 2465297 | 7/2003 |
| CA | 2525935 | 11/2004 |
| JP | 2002351727 | 12/2002 |
| WO | WO 00/33350 | 6/2000 |
| WO | WO 2072863 A2 * | 9/2002 |

OTHER PUBLICATIONS

Whitehouse et al., Electrospray Interface for Liquid Chromatographs and Mass Spectrometers, Analytical Chemistry, vol. 57, 1985, pp. 675-679 (5 pages).

Thomson, et al., Improved Collisionally Activated Dissociation Efficiency and Mass Resolution on a Triple Quadropole Mass Spectrometer System, Analytical Chemistry, vol. 34, 1, pp. 1696-1704 (9 pages).

Morris, et al., Characterization of High Pressure Quadropole Collision Cell for Low-Energy Collision Induced Dissociation, J. Am. Soc. Mass Spectrum, vol. 5, 1994, pp. 1042-1063.

Jones, et al., Sequence Dependence of Peptide Fragmentation Efficiency Curves Determined by Electrospray Ionization/Surface-Induced Dissociation Mass Spectrometry, Journal of the Americam Chemical Society, No. 116, 1994, pp. 8368-8369 (2 pages).

Curcuroto, et al., Effects of Target Identity and Collision Energy on the Fragmentation of Some Mass-selected Protonated Neuropeptides, Rapid Communications in Mass Spectrometry, vol. 7, 1993, pp. 989-993 (5 pages).

Borda-Nagy, et al., Collision-Induced Decomposition of Ions, Int. Journal of Mass Spectrometry and Ion Process, vol. 100, 1990, pp. 105-131 (27 pages).

* cited by examiner

SYSTEM AND METHOD FOR DATA COLLECTION IN RECURSIVE MASS ANALYSIS

CROSS-REFERENCE TO RELATED APPLICATIONS

This application claims the benefit of U.S. provisional patent application Ser. No. 60/686,918, filed 3 Jun. 2005 and entitled System and Method for Data Collection in Recursive Mass Analysis.

FIELD OF THE INVENTION

The invention relates generally to data collection, and more particularly to systems and methods for data collection and processing in recursive mass analysis of particles.

INTRODUCTION

Mass spectrometry, also called mass spectroscopy, is an instrumental approach that allows for the mass measurement of molecules. Mass spectrometers have become pivotal for a wide range of applications in the analysis of inorganic, organic, and bio-organic chemicals. Examples include dating of geologic samples, drug testing and drug discovery, process monitoring in the petroleum, chemical, and pharmaceutical industries, surface analysis and the structural identification of unknowns. Further, mass spectrometry is being continually improved and has recently had significant advances in its application to molecular biology, where it is now possible to analyze proteins, DNA, and even viruses.

A mass spectrometry system typically includes an ion source, a mass analyzer, and a data collection device interfaced with or integral to a computer, data processor, or other controller. The combination of such devices enables a mass spectrometer to determine the molecular weight of chemical compounds by ionizing, separating, and measuring molecule-sized particles according to their mass-to-charge ratios (m/z). Ions may be generated in the ionization source by inducing either the loss or the gain of charge (e.g. electron ejection, protonation, or deprotonation). Once ions are formed they can be directed into a mass analyzer and detected. The ionization and detection of a mass using a mass spectrometer can be used to generate a mass-to-charge ratio ("m/z") spectrum that can provide molecular weight information.

A high resolution mass spectrometer can typically detect ions of hundreds of thousands of possible mass-to-charge ratios. Typically, data collected during a scan is stored in volatile or persistent memory in a large array-type data structure having hundreds of thousands of bins, or unique addresses, each bin associated with an identifier corresponding to a possible mass-to-charge ratio that can be detected by the spectrometer. As data is received during a scan, bins corresponding to detected mass-to-charge ratios are incremented to reflect the detection. This approach allows for and indeed requires the use of enough memory to hold the largest possible spectrum. However, in a typical scan, only 20% of the total spectrum range is actually detected. Hence, a scan is generally followed by a compression procedure in which the array holding the scan results is compressed to eliminate those bins which hold intensity values below a desired threshold—for example, those bins for which the ions associated with the corresponding m/z ratios have not been detected.

For example, during a typical scan using a spectrometer adapted for time-of-flight (TOF) mass analysis, a spectrometer will maintain an array of up to 500,000 bins. This can then result in 500,000 post-scan iterations to compress the array to a more manageable mass intensity pair list which requires significantly less memory for storage. The storage and processing demands of a scan can increase dramatically where a scan needs to be acquired in multiple segments or at higher rates. For example, if a scan has 3 segments and is to be acquired recursively at intervals of 0.3 second using prior art techniques, then effectively 3*500,000/0.3 post-scan iterations will be performed to compress the array. Compressions involving arrays of such magnitude can require relatively large amounts of processor resources, and therefore can impose relatively long times between scans. Such post-scan processing can therefore result, for example, in missed scanning opportunities, in which compounds of interest are potentially lost.

SUMMARY OF THE INVENTION

The invention provides systems, methods, and computer programming useful for the collection, storage, and other processing of data acquired in mass analyses using mass spectrometers.

According to an aspect of the invention there is provided a method of collecting data using a mass spectrometer comprising a particle detector or other mass analyzer. A data collection such as a tree or array structure which includes bins for storing detected data is maintained in volatile or persistent memory. Data is received from the detector. Whether the collection contains a bin corresponding to a received data record is determined. If the collection does not contain a bin corresponding to the received data record, a bin corresponding to the data record is added. In either case, the bin corresponding to the received data record is then updated to reflect its reception.

In related aspects, the invention provides methods of recording data acquired by mass analyzer in data sets comprising pluralities of data records. The data records comprise unique identifiers associated with corresponding mass-related data signals and counters. The methods are performed by data processor communicatively linked to the mass analyzers, and comprise receiving mass-related data signals and determining unique identifiers associated with the mass-related data signals, such as mass-to-charge ratios and/or times of flight of ions detected by the mass analyzers. If the unique identifiers associated with the mass-related data signals correspond to unique identifiers of existing data records, counters associated with the existing data records are increased, so that for example the number of corresponding data signals received by the data processor may be counted. If the identifiers associated with the newly-acquired data signals do not correspond to identifiers of existing data records, new data records comprising the new identifiers are created. Data sets so created may be stored in volatile and/or persistent memories associated with the data processors.

In other aspects, the invention provides computer programming media and systems for creating data sets in accordance with such methods.

BRIEF DESCRIPTION OF THE DRAWINGS

The invention will now be described by way of example only, and with reference to the accompanying drawings, in which.

DETAILED DESCRIPTION OF THE INVENTION

Figure 1:
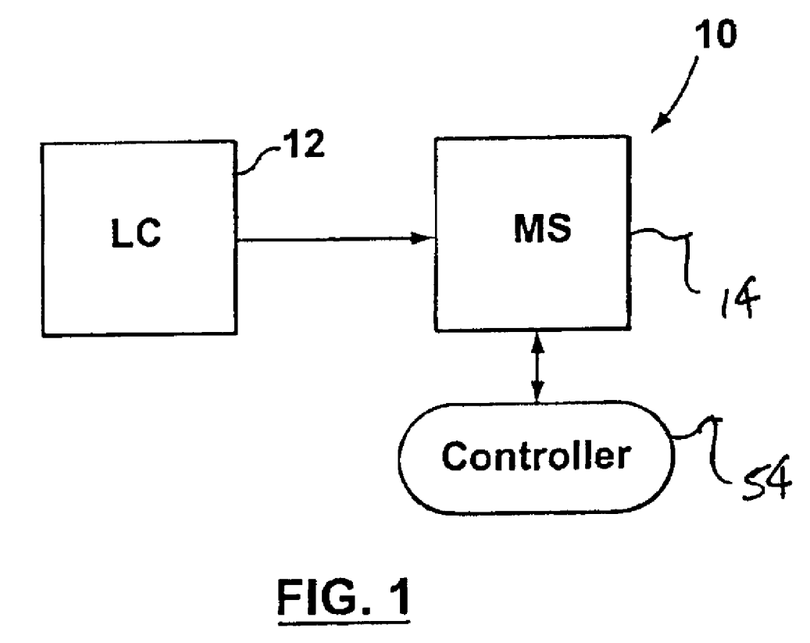
FIG. 1 is a schematic block diagram of a mass spectrometry system suitable for use in implementing the invention.

FIG. 1 shows basic components of a mass spectrometry system 10 suitable for use in implementing the invention. System 10 comprises ion source 12, including for example a liquid chromatography column, 12 coupled to a mass spectrometer 14 capable of conducting multiple stages of mass spectrometry. Examples of such a system include the QSTAR®, API 3000™ and API 4000™ LC/MS/MS systems marketed by MDS Sciex, although those skilled in the art will appreciate that the invention can be implemented using any suitably-controlled system that has MS and MS/MS or other multi-MS capabilities (e.g., a 3D trap or time-of-flight (TOF) analyzer). Data acquisition controller 54 enables automated MS to MS/MS acquisition for maximum efficiency of extraction of information from a single or multiple LC/MS runs.

Controller 54 is adapted for receiving, storing, and/or otherwise processing data signals acquired or otherwise provided by mass spectrometer 14, and for providing command signals adapted for the control of operations performed by mass spectrometer 14. Controller 54 can further provide a user interface suitable for controlling the MS system 10, including for example input/output devices suitable for accepting from the user and implementing system commands, displaying and otherwise controlling output, etc. In particular, controller 54 can be adapted for processing data acquired by mass spectrometer 14 and providing to mass spectrometer 14 command signals for use in controlling mass analyses conducted by the spectrometer, determined at least in part on information generated by the processing of such data.

Controller 54 can comprise any data-acquisition and processing system(s) or device(s) suitable for use in accomplishing the purposes described herein. Controller 54 can comprise, for example, a suitably-programmed or -programmable general- or special-purpose computer, or other automatic data processing equipment, with associated programming and data acquisition and control devices. Controller 54 can be adapted, for example, for controlling and monitoring ion detection scans conducted by mass spectrometer 14; and for acquiring and processing data representing such detections by mass spectrometer 14 of ions provided by, for example, liquid chromatography (LC) column 12, as described herein.

Accordingly, controller 54 can comprise one or more automatic data processing chips adapted for automatic and/or interactive control by appropriately-coded structured programming, including one or more application and operating system programs, and any necessary or desirable volatile or persistent storage media. As will be understood by those skilled in the relevant arts, a wide variety of processors and programming languages suitable for implementing the invention are now available commercially, and will doubtless hereafter be developed. Examples of suitable controllers, comprising suitable processors and programming are those incorporated in the QSTAR®, API 3000™ and API 4000™ LC/MS/MS systems available through MDS Sciex of Ontario, Canada.

Ion sources suitable for use in implementing the invention can comprise any LC column or other ion source 12 compatible with the purposes disclosed herein. For example, as will be apparent to those skilled in the relevant arts, any liquid chromatography or other sustained-release ion source(s) will serve. The invention can be particularly effective when implemented in combination with LC columns and other ion sources that produce sustained or other streams of ions of varying character.

Mass spectrometer 14 can comprise any ion detector and/or other mass analyzer(s) compatible with the purposes disclosed herein. For example, as will be apparent to those skilled in the relevant arts, 3D ion traps, TOF detectors, and other types of mass spectrometers will serve. The invention is particularly useful in combination with mass spectrometers capable of repeated or recursive scans or other samplings of ion groups.

Mass spectrometer 14 comprises a detector that allows mass spectrometer 14 to generate data signals signal in accordance with the ions that have been detected. Such data signals generally include mass-related signals corresponding directly or indirectly to characteristics of ions detected by the mass analyzer(s) comprised by mass spectrometer 14. For example, according to an embodiment in which a TOF process is used for mass analysis, different ions reach the detector at different times. For example, smaller ions can reach the detector first because of their greater velocity and larger ions can take longer. Thus, m/z may determined according to an ions' time of arrival at the detector, through the use of mass-related data signals representing the time of flight of the ions within the TOF mass analyzer.

Figure 2:
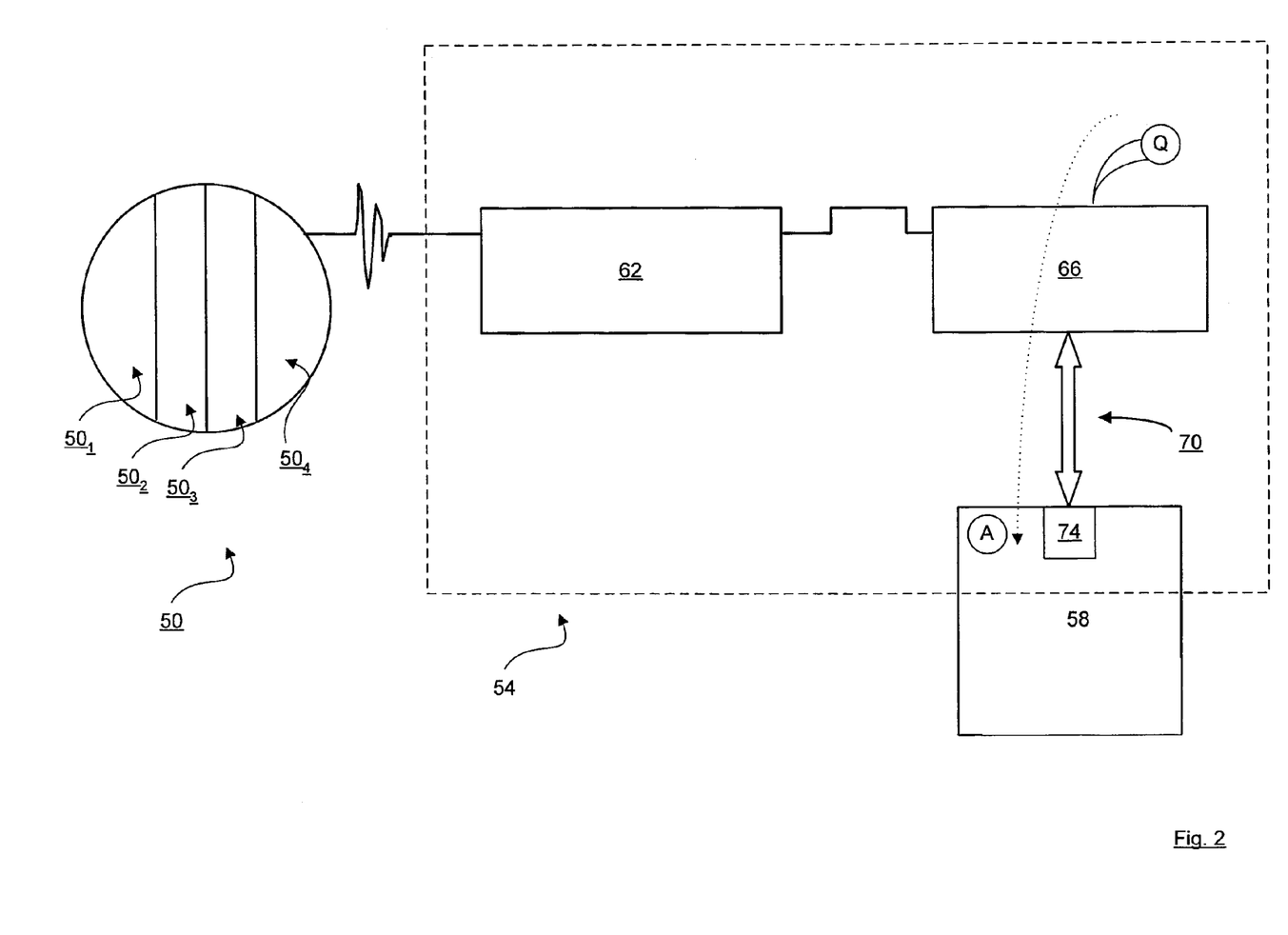
FIG. 2 is a schematic block diagram of a controller suitable for use in implementing the invention.

Referring to FIG. 2, a controller 54 and its relation to a mass detector 50 of mass analyzer 14 is shown in greater detail. In an example embodiment detector 50 of mass spectrometer 14 comprises a four-anode detector, each anode shown as $50_1$, $50_2$, $50_3$ and $50_4$, such as is often incorporated in a TOF mass analyzer; a constraint fraction discriminator (CFD) 62; a time digital converter (TDC) 66, and signal collection device 58 When one or more ions strike any of the four anodes $50_1$ through $50_4$, they cause an electron cascade which generates corresponding pulses, i.e., a mass-related data signals, which can be sent though a constant fraction discriminator (CFD) 62. In other embodiments, detector 50 can operate by inducing a current generated by a moving charge to produce such signals. In yet other embodiments detector 50 can include an electron multiplier, or a scintillation counter, and convert the kinetic energy of incident ions into a cascade of secondary electrons to provide such signals. These and all other suitable types of detectors are within the scope of the contemplated invention.

It has been found that NIM, TTL, and other pulses serve well for providing data signals suitable for use in implementing the invention. NIM signals can be triggered, for example, at −0.8 volts, while TTL signals generally provide +5 volt signals.

For many types of analysis now conducted using systems according to the invention, NIM pulses are found to be particularly efficient, particularly where high speed is required. Thus in one presently-implemented embodiment, the output signal from CFD 62 is a single-15 nanosecond NIM pulse which is routed into the time digital converter (TDC) 66. In other embodiments the mass-related signal output of CFD 62 can take different forms. TDC 66 stores the time of arrival relative to the pusher pulses in mass analyzer 46 in a short (First In First Out) FIFO queue Q.

A number of CFDs suitable for use in implementing the invention are now available commercially. One example is the Ortec 975 Quad CFD, which provides a pulse width or signal duration of approximately 5-20 nanoseconds. For many types of analysis using equipment of the type described herein, 15-nanosecond pulses have been found to serve well.

A number of TDCs suitable for use in implementing the invention are currently available commercially. One example that has been used successfully is provided by Ionwerks. It is noted that ADCs are also suitable for use in implementing the invention, particularly where suitable hardware or digital signal processing (DSP) thresholding is applied to data signals provided by the mass analyzer.

In the example shown, connection 70 transfers the arrival time signals from the FIFO queue in TDC 66 to an input device 74 located in or otherwise communicatively associated (i.e., communicatively linked) with signal collection device 58. In a present embodiment, input device 74 comprises a HotLink high speed serial controller and connection 70 comprises a HotLink high speed serial cable operable to connect properly equipped peripherals to computing devices. In other embodiments, input device 74 can comprise other types of input controllers, such as a FireWire, universal serial bus (USB) or high speed parallel port controller; and connection 70 can include other types of cables or connections that are suitable for the type of input device used. Referring back to FIG. 2, a single mass-related data signal representing time of flight stored in queue Q is depicted as oval A, and its movement in the system is shown by the dotted arrow. In a present embodiment, the digitized data includes a value representing the arrival time of an ion and is represented as the oval A in FIG. 2.

Figure 3:
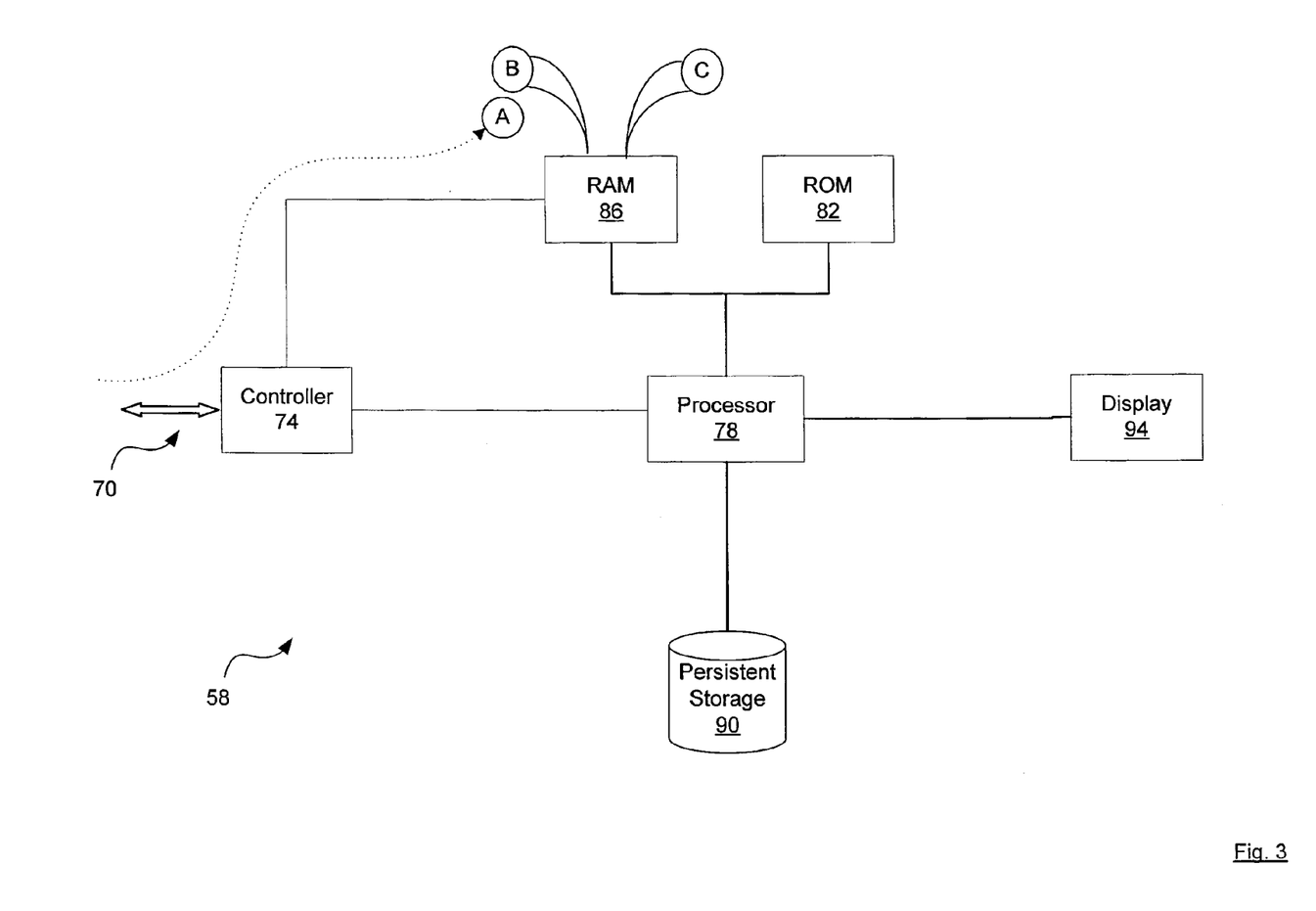
FIGS. 3 and 4 are schematic block diagrams of components suitable for use in implementing the invention.

Referring now to FIG. 3, a block diagram of internal components useful in implementing a data collection device 58 are shown. In a present embodiment, the collection device 58 comprises a standard dual processor micro computer such as a Dell Precision 670 manufactured by Dell corporation of Round Rock, Tex. It should be noted that in other embodiments, other types of equipment such as single or multiple processor micro computers, mini computers, or dedicated proprietary electronic boards could be used as collection device 58. Any computer or other data processor suitable for use in accomplishing the purposes disclosed herein will serve.

In the embodiment illustrated in FIG. 3, device 58 includes at least one processor 78. Processor 78 is connected to a read-only-memory ("ROM") 82, which can store programming media suitable for use in causing processor(s) 78 to execute a plurality of applications that enable device 58 to perform the various functions disclosed herein. Processor(s) 78 are also connected to a random access memory unit ("RAM") 86 and a persistent storage device 90 which is responsible for various non-volatile storage functions of device 58. Processor 78 can send output signals to various output devices including display 94. Processor(s) 78 can comprise any digital signal processors suitable for use in implementing the processes disclosed herein.

Device 58 can also receive data from connection 70 through controller 74 as described above, so that for example processor(s) 78 are communicatively linked, via any intermediate devices such as TDC 66 and/or CFD 62, to detector 50 of mass analyzer 14. Thus controller 54 and/or processor(s) 78 are operable, among other purposes, to transfer the mass-related data signals received from mass analyzer 14 directly to RAM 86. In some embodiments, controller 54 is operable to transfer the data signals to RAM 86 directly, without going through processor 78. In a present embodiment controller 54 further is operable to access memory directly using the direct memory access (DMA) protocol. In other embodiments, other protocols could be used for accessing RAM 86 directly. Accordingly, in a present embodiment, controller 54 receives time data A through connection 70. Referring back to FIG. 3, controller 54 is operable to move data A into a first in first out (FIFO) buffer B which can reside in memory 60. In a present embodiment, buffer B is 2 megabytes, but in other embodiments size buffer B can be varied according to various parameters such as length of scan, speed of data arrival into buffer B, and speed of removal of data from buffer B. All these and other variations are within the scope of the invention.

Thus, as will be understood by those skilled in the relevant arts, processor(s) 78 can receive mass-related data signals from the mass analyzer 14 and determine unique identifiers corresponding to characteristics of the data signals. For example, using appropriate mathematical relations, which are well known to those skilled in the relevant arts, data signals representing time of flight within a TOF mass analyzer can be converted to values representing mass-to-charge ratios, each distinct m/z ratio being useful as a unique identifier associated with a data record corresponding to that m/z ratio and useful for determining a number, or charge intensity, of ions of that m/z ratio detected by mass analyzer 14, as described herein.

Figure 4:
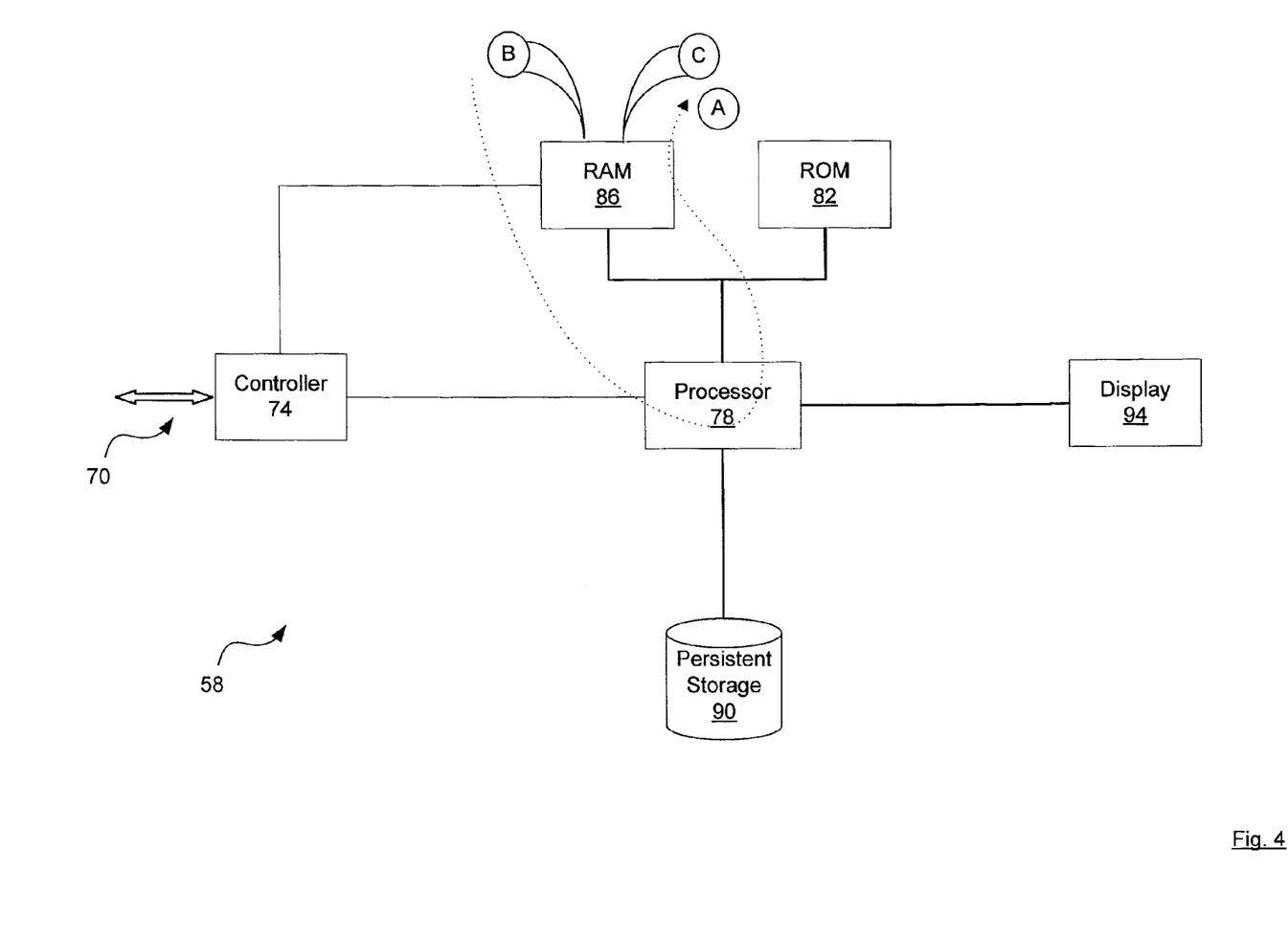

Referring now to FIG. 4, device 58 also assembles and maintains in RAM 86 a collection or set C of data which can include, for example, data records corresponding to or otherwise associated with data signals provided by or otherwise acquired from mass spectrometer 14, as described herein. Data signals from buffer B can, for example, be transferred into set C from mass spectrometer 14 during the course of an ion scan. In a present embodiment, each scan typically lasts from approximately 100 milliseconds to 2000 milliseconds. Accordingly, in a present embodiment, set or collection C contains a spectrum of values representing ion arrival times corresponding to a m/z spectrum that can be collected by spectrometer 14 during a 100- to 2000-millisecond scan. Moreover, in a present embodiment, the resolution of spectrometer 14 can be such that up to 5,000,000 distinct possible arrival time values at which ions can be detected in a scan.

Figure 5:
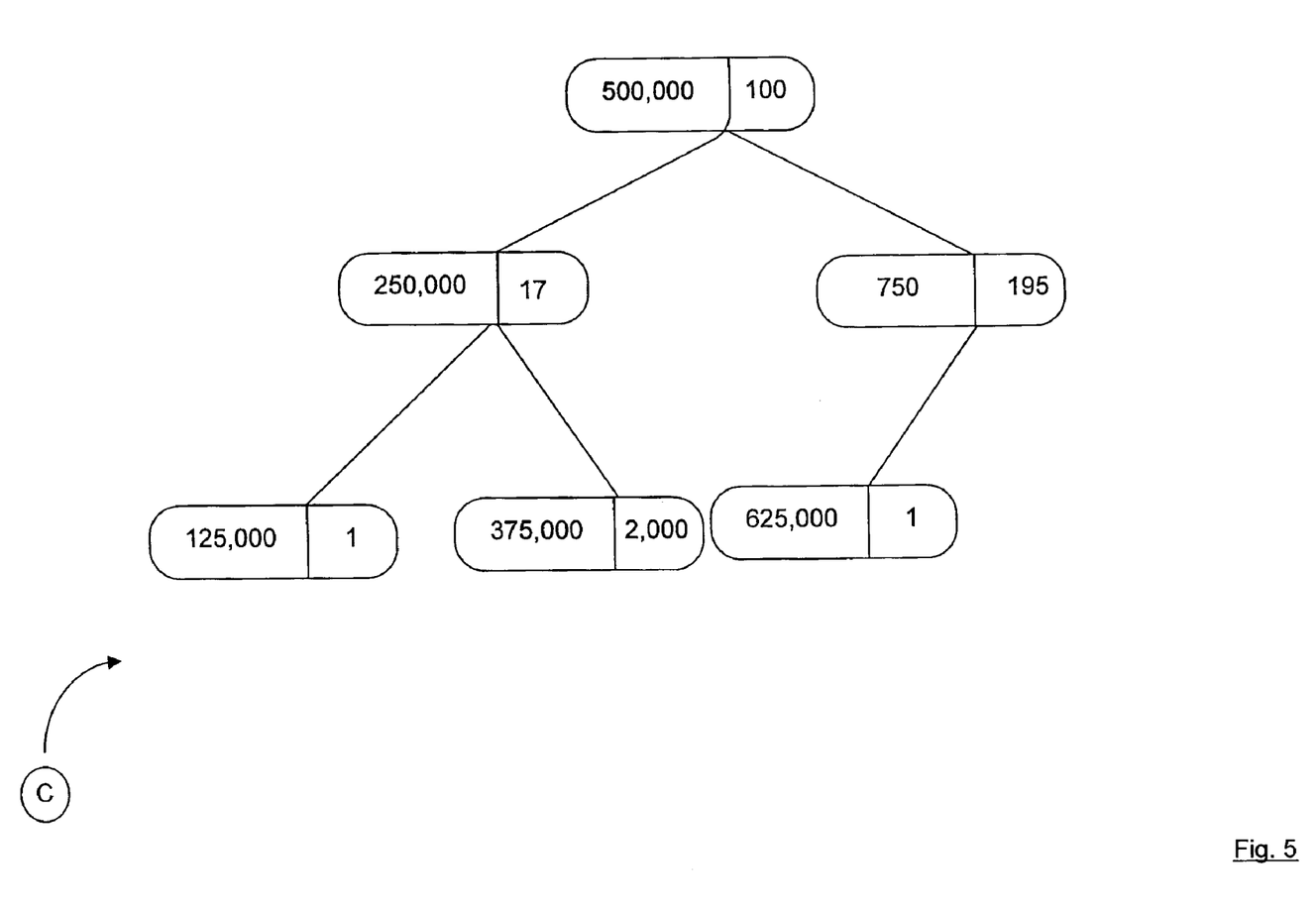
FIG. 5 is a schematic diagram of a data set accordance with the invention.

As will be appreciated by those skilled in the relevant arts, once they have been made familiar with this disclosure, data set C can be implemented in a wide variety of ways. In one presently-implemented embodiment, for example, data set C is implemented in the form of a binary tree. For example, collection C can be implemented using binary tree templates provided in Standard Template Libraries (STL) as published by SGI Inc. As shown in FIG. 5, each node, or data record, of binary tree collection C comprises two elements corresponding characteristics of a mass-related data signal acquired from mass spectrometer 14, namely, in the example shown, to mass intensity pairs comprising mass-to-charge ratios and cumulative signal intensity. The left element, in the embodiment illustrated, comprises a value representing arrival time values, which correspond to m/z ratios, and are also used as keys, i.e., as unique data signal identifiers. The right element stores an ion count associated with that arrival time value. In a present embodiment, the data in binary tree collection C is stored according to known binary tree protocols, in an ordered fashion according to the key, or unique identifier, e.g., m/z ratio. For example, the left descendant or child of a node has a larger key value than the right descendant. It should be noted, however, that in other embodiments, other data structures such as hash tables, and linked lists can also be used. All data structures consistent with the purposes and processes disclosed herein are considered to be within the scope of the invention.

Figure 6:
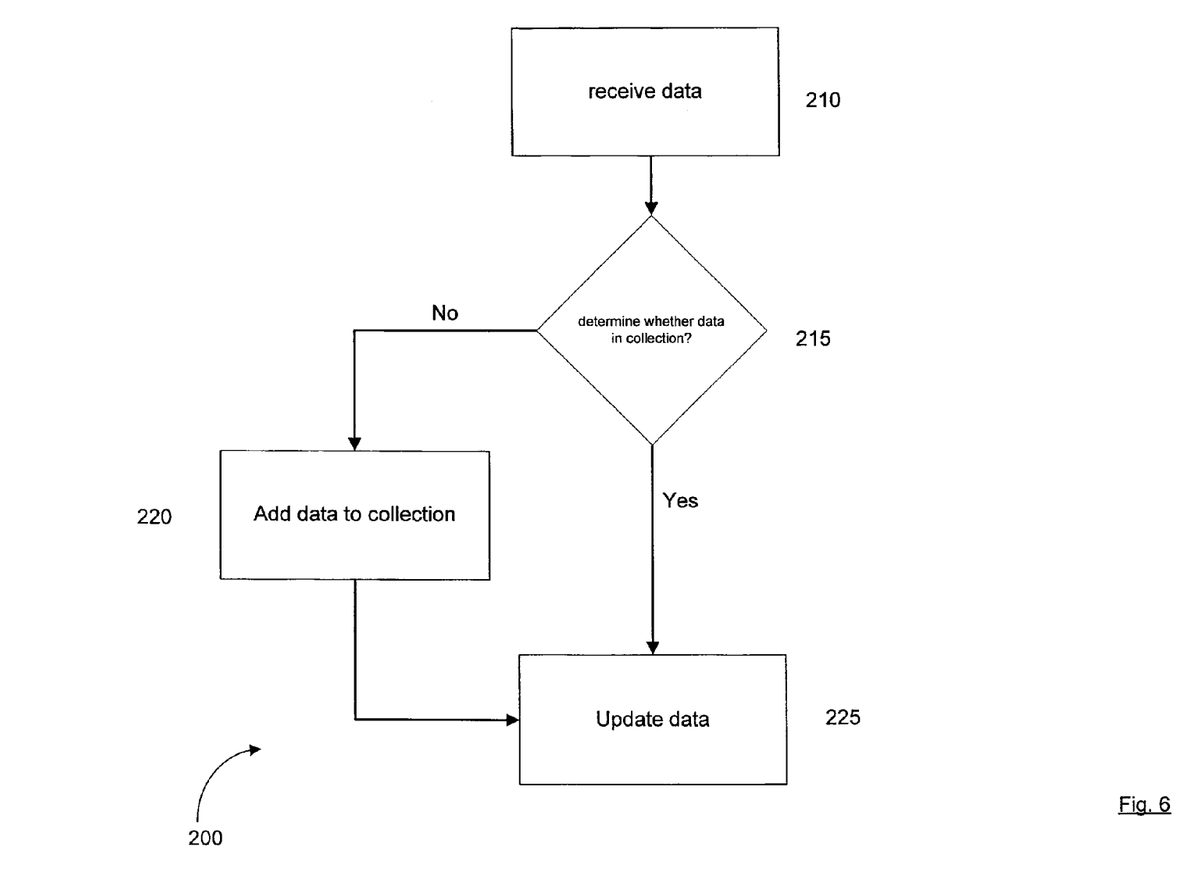
FIG. 6 is schematic flow chart of a method for collecting data in accordance with the invention.

Referring now to FIG. 6, a method for collecting data using a mass spectrometer scan is indicated generally at 200. In order to assist in the explanation of the method, it will be assumed that method 200 is performed by a system 10 including a spectrometer 14, as described herein. Furthermore, the following discussion of method 200 will lead to further understanding of system 30 and its various components. However, it is to be understood that system 10 and/or method 200 can be varied, and need not work exactly as discussed herein in conjunction with each other, and that such variations are within the scope of the present invention.

At the beginning of a scan, binary tree data set C is empty. Performance of method 200 can start at any time during a scan or after a scan is complete, as for example where all scanned data is stored in a suitable buffer. In a present embodiment, performance of method 200 starts as soon as data is available in buffer B. To simplify the explanation of the method, however, it will be assumed that a scan has already started and collection C has already received a number data points and has been built up to the point shown in FIG. 5.

Figure 7:
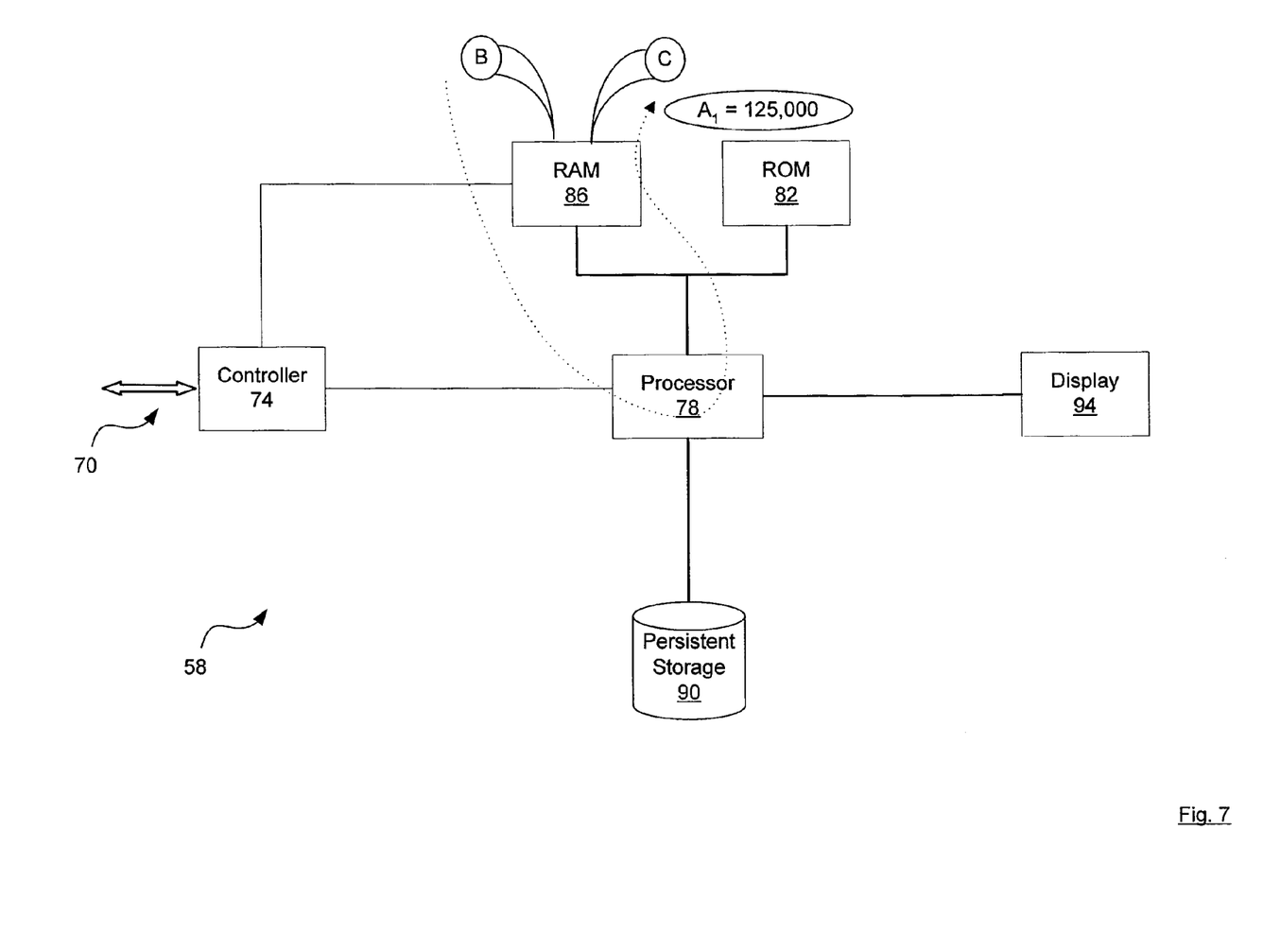
FIG. 7 is a schematic block diagram of components suitable for use in implementing the invention.

Referring back to FIG. 6, at 210 a mass-related data signal is received by a processor(s) 78 from mass analyzer 14. As shown in FIG. 7, in a present embodiment, data signal $A_1$, which represents an arrival time value of 875,000, is read from buffer B by the processor(s) 78 and becomes the received data. At 215, it is determined whether any data record comprising information corresponding to the time value 875,000, which may be used within the data set as a unique identifier of a corresponding data record, already exists within data set C. Specifically, collection C is searched to determine whether a node, or data record, corresponding to the key value or unique identifier of 875,000 exits. In the current example, such a node does not exist, and processor(s) 78 proceed to step 220 of method 200.

Figure 8:
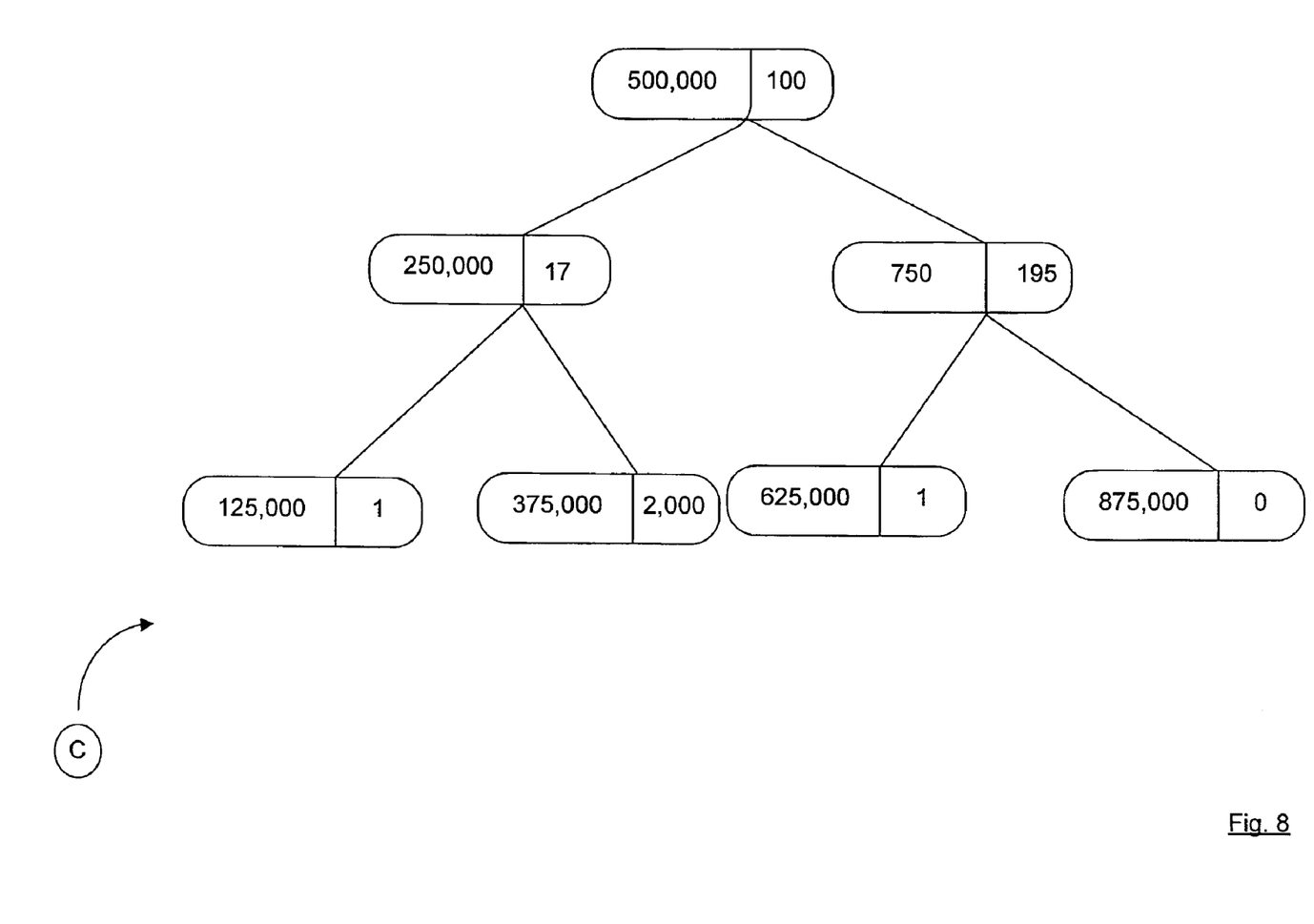
FIGS. 8-10 are schematic diagrams of data sets accordance with the invention.
Figure 9:
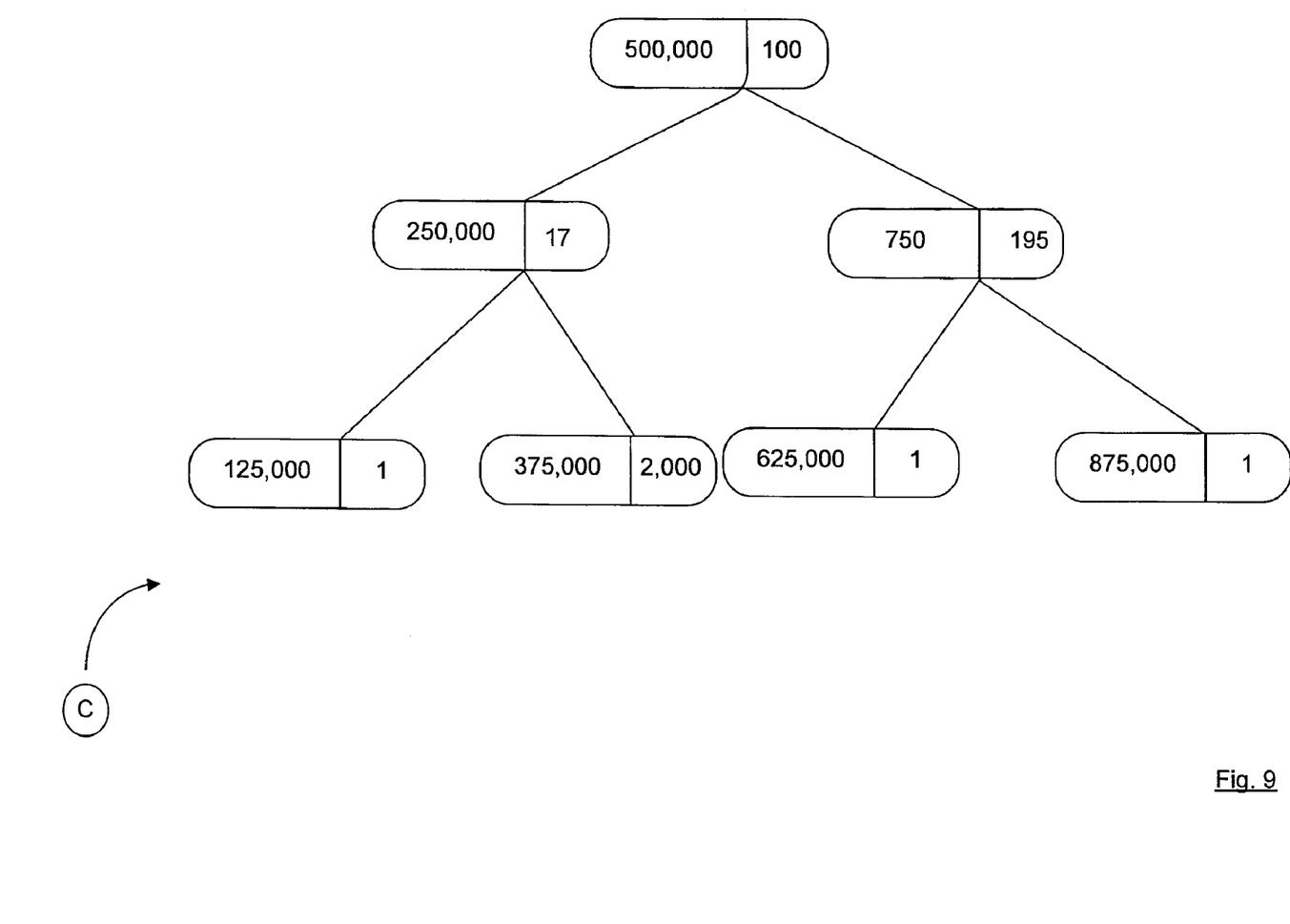

No corresponding data record being found within the existing data set, at 220 a new node is added. Specifically, as shown in FIG. 8, a node corresponding to time value (and thus key) 875,000 is added. Also, shown in FIG. 8, the newly-created data record 804 comprises an associated counter value with an initial value of 1. At 225, node 804 corresponding to the newly-received data signal is updated. Specifically, as shown in FIG. 9, the counter of the node is incremented to reflect that an ion with the corresponding time, m/z, or other mass-related value has been received.

Figure 10:
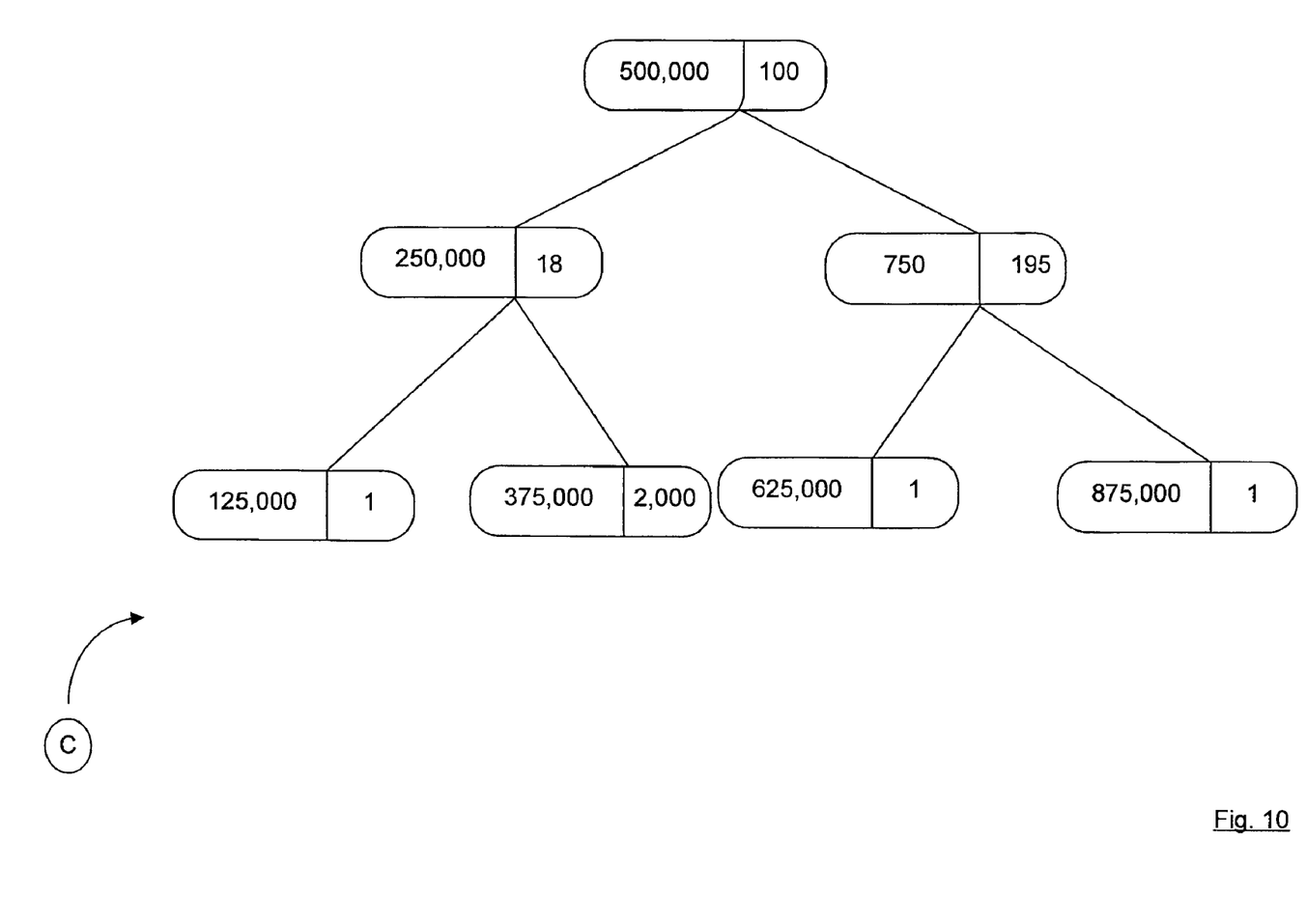

In another performance of method 200, it can be assumed that a data signal received at 210 corresponds to time value 250,000. Accordingly, as shown in FIG. 9, during the performance of 215 it will be determined that a data record or node 806 corresponding to the received signal already exists, advancing the performance of method 200 to 225, thus skipping the performance of 220. Performance of 225 can then result in the increment of count value at node 250,000, as shown in FIG. 10, from a value of 17 to a value of 18.

Performance of method 200 can be repeated as many times as there are data signals in buffer B. In an example embodiment, a data signal is received from buffer B every 5 milliseconds. However, as it will be apparent to those skilled in the art, the frequency of method 200's performance can be adjusted according to various parameters such as scan speed, speed of processing and connection speeds. These and other variations are within the scope of the invention.

In other aspects, the invention provides computer programming media adapted for causing one or more data processors to record data acquired by a mass analyzer in accordance with the methods and processes described herein. As will be readily appreciated by those skilled in the relevant arts, a wide variety of programming languages and structures may be used to implement the invention. For example, assembly language codes or high-level languages such as any of the C variants, FORTRAN, or COBOL could be used to implement a wide variety of suitable routines, modules, and applications comprising suitably-adapted machine instructions. The selection of suitable language and programming structure combinations will not trouble those skilled in the relevant arts, when they have been made familiar with this disclosure.

While only specific combinations of the various features and components of the present invention have been discussed herein, it will be apparent to those of skill in the art that subsets of the disclosed features and components and/or alternative combinations of these features and components can be utilized, as desired. For example, a scan can comprise multiple segments, each requiring a different collection C. Moreover, spectrometer 14 could contain multiple detectors, as in the case of a quadripole spectrometer, each feeding data into separate channels in one controller or a single channel in separate controllers. Each of these channels can then feed data into a different buffer, and the data from different buffers can be collected in different collections C. Hence a scan can yield multiple data collections C. For example, if a spectrometer has four detectors and a scan is completed in 3 segments, a total of 12 separate collections C will be generated per scan.

In further variations, detected data signals could include an intensity value representing the detector response caused by single ions, or by groups of ions detected simultaneously. Accordingly, data signal A transmitted to collection C would have an additional associated value corresponding to a value by which to increment the counter of a node 804.

In yet another variation there may be no buffers, and method 200 could be applied to data as they are received by input device 74.

The above-described embodiments of the invention are intended to be examples of the present invention and alterations and modifications may be effected thereto, by those of skill in the art, without departing from the scope of the invention which is defined solely by the claims appended hereto. The invention is therefore not to be limited to the exact components or details of methodology or construction set forth above. Except to the extent necessary or inherent in the processes themselves, no particular order to steps or stages of methods or processes described in this disclosure, including the Figures, is intended or implied. In many cases the order of process steps may be varied without changing the purpose, effect, or import of the methods described.

What is claimed is:

1. A method of recording data acquired by a mass analyzer in a data set comprising a plurality of data records, the data records comprising unique identifiers associated with corresponding mass-related data signals and counters, the method performed by a data processor communicatively linked to the mass analyzer and comprising:

a. receiving a mass-related data signal;

b. determining a unique identifier associated with the mass-related data signal;

c. if the unique identifier associated with the mass-related data signal corresponds to a unique identifier of an existing data record, incrementing a counter associated with the data record;

d. else, creating a data record comprising the unique identifier and an associated counter.

2. The method of claim 1, comprising storing the data set in persistent memory.

3. The method of claim 1, wherein the mass-related data signal represents a mass-to-charge ratio of an ion detected by the mass analyzer.

4. Computer programming media adapted for causing a data processor to record data acquired by a mass analyzer in a data set comprising a plurality of data records by causing the data processor to:
   a. receive a mass-related data signal;
   b. determine a unique identifier associated with the mass-related data signal;
   c. if the unique identifier associated with the mass-related data signal corresponds to a unique identifier of an existing data record, increment a counter associated with the data record;
   d. else, create a data record comprising the unique identifier and an associated counter.

5. The programming media of claim 4, adapted for causing the data processor to store the data set in persistent memory.

6. A system useful for recording data, comprising:
   a mass analyzer adapted to detect ions provided by an ion source;
   a processor and memory associated with the processor, the processor adapted to:
   a. receive a mass-related data signal;
   b. determine a unique identifier associated with the mass-related data signal;
   c. if the unique identifier associated with the mass-related data signal corresponds to a unique identifier of an existing data record, increment a counter associated with the data record;
   d. else, create a data record comprising the unique identifier and an associated counter.

7. The system of claim 6, wherein the mass-related data signal represents a mass-to-charge ratio of an ion detected by the mass analyzer.

8. The system of claim 6, wherein the mass analyzer comprises a time-of-flight mass analyzer.

9. The system of claim 8, wherein the mass-related data signal corresponds to a time of flight of an ion detected by the mass analyzer.

10. The system of claim 6, wherein the ion source comprises a liquid chromatography column.

* * * * *